US00PP31767P2

(12) United States Plant Patent
Hansen

(10) Patent No.: US PP31,767 P2
(45) Date of Patent: May 12, 2020

(54) ***SEDUM* PLANT NAMED 'BOOGIE WOOGIE'**

(50) Latin Name: ***Sedum kamtschaticum* (Fisch.)**
Varietal Denomination: Boogie Woogie

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/501,323

(22) Filed: Mar. 26, 2019

(51) Int. Cl.
*A01H 5/12* (2018.01)
*A01H 6/32* (2018.01)

(52) U.S. Cl.
USPC ..... Plt./479

(58) Field of Classification Search
USPC ..... Plt./479
See application file for complete search history.

*Primary Examiner* — Susan McCormick Ewoldt

(57) ABSTRACT

The new and distinct cultivar of perennial *Sedum* plant named 'Boogie Woogie' is characterized by drought-tolerant, winter-hardy, tight, low, clumps, flower stems that remain upright in the center of the plant throughout the growing season, small, medium-green, glossy foliage with variegated margin of cream blushed with reddish-purple and numerous bright yellow flowers clustered on small heads that completely covering the compact, low-mounded plant.

1 Drawing Sheet

Botanical designation: *Sedum kamtschaticum* (Fisch.).
Cultivar denomination: 'Boogie Woogie'.

STATEMENT REGARDING PRIOR DISCLOSURES UNDER 37 CFR 1.77(b)(6)

The first public disclosure of the claimed plant, was the non-enabling photograph and brief description on a website operated by Walters Gardens, Inc. on Dec. 1, 2018. Prior to that the claimed plant was first sold privately on Apr. 23, 2018 by Walters Gardens, Inc., who obtained the plant and all information relating thereto, from the inventor. No plants of *Sedum* 'Boogie Woogie' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Sedum* or stonecrop plant, botanically known as *Sedum* and hereinafter referred to by the cultivar name 'Boogie Woogie'. The new plant is a discovery by the inventor of a naturally occurring branch sport mutation at a wholesale perennial nursery production field in Hamilton, Mich., USA of *Sedum kamtschaticum* 'Little Miss Sunshine' U.S. Plant Pat. No. 30,039 on Aug. 13, 2017. The individual plant originating from the branch sport selection was given the breeder code 17-SP-SED-607 during the evaluation process at the trial gardens at Zeeland, Mich. of the same nursery.

The new *Sedum* plant was selected for its compact groundcover habit form together with the cheery, bright-yellow flower color and particularly the dark green foliage with broad, creamy-white, marginal variegation.

Asexual reproduction of *Sedum* 'Boogie Woogie' by vegetative cuttings at a wholesale perennial nursery in Zeeland, Mich., USA since the Aug. 13, 2017, has shown that the unique features of this new *Sedum* plant are stable and reproduced true to type in successive generations.

SUMMARY OF THE INVENTION

Plants of *Sedum* 'Boogie Woogie' have not been observed under all possible environmental conditions. The phenotype may vary somewhat with variations in environment such as temperature, available water, fertility and light intensity without, however, any variation in genotype.

The following traits have been repeatedly observed and are determined to be the unique characteristics of *Sedum* 'Boogie Woogie'. The following characteristics in combination distinguish 'Little Miss Sunshine' as a new and distinct *Sedum* plant unique from all other Stonecrop plants known to the inventor:

1. Short and compact plant habit.
2. Small, medium-green, glossy foliage produced on short stiff stems.
3. Leaf margins are creamy developing slight reddish blush in high light conditions.
4. Stems develop a reddish-purple blush in high light.
5. Numerous, bright yellow flowers in clusters nearly completely cover the plant in early summer.
6. Plants are drought tolerant and winter hardy to at least USDA zone 3.

In comparison to sport parent, 'Little Miss Sunshine', the new plant has foliage with a broad creamy margin, a slightly lighter green center, and foliage and stems take on a reddish to reddish-purple blush.

Other similar plants include *Phedimus* 'Nonsitnal' U.S. Plant Pat. No. 27,454 and *Sedum kamtschaticum* 'Variegatum' (not patented). 'Nonsitnal' has pinkish buds and the fruit develops a pinkish color. The foliage of 'Nonsitnal' is more sharply dentate. *Sedum kamtschaticum* 'Variegatum' has foliage with a thinner creamy margin and the fruit develops a pinkish-orange coloration. *Sedum kamtschaticum*

'Variegatum' is also larger in habit, with larger leaves and produces fewer flowers that are larger than the new plant.

BRIEF DESCRIPTION OF THE PHOTOGRAPH

The photograph of the new plant demonstrates the unique traits and the overall appearance of *Sedum* 'Boogie Woogie'. The colors are as accurate as reasonably possible with color reproductions of this type. Variations in ambient light spectrum, source and direction may cause the appearance of minor variation in color. The plants used in the photographs were one-year-old plants grown in an open, full-sun trial garden at a wholesale perennial nursery in Zeeland, Mich. with supplemental water and fertilizer when needed. No plant growth regulators have been used.

DETAILED BOTANICAL DESCRIPTION

Figure 1:
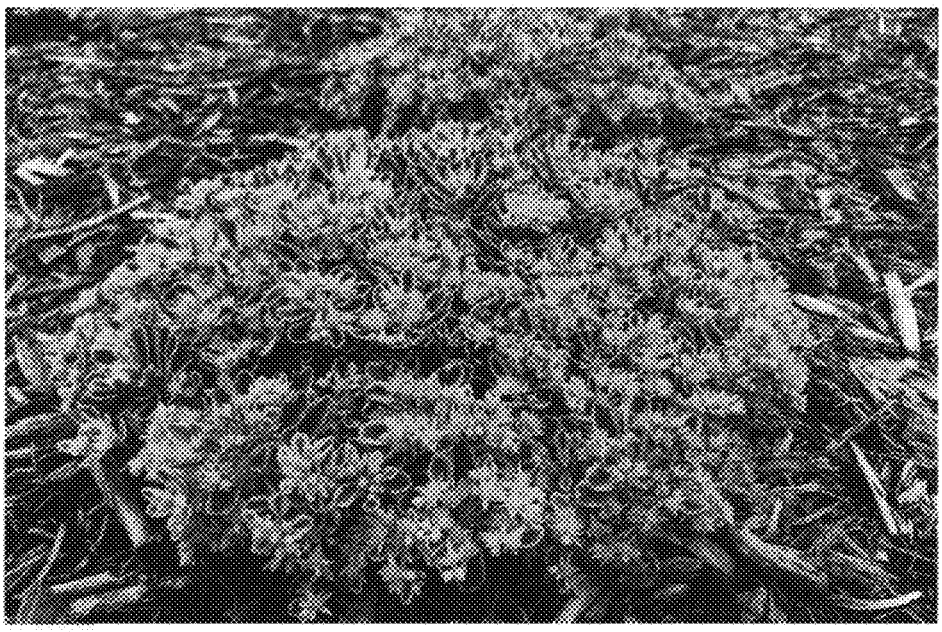
FIG. 1 shows the plant in full flower habit.
Figure 2:
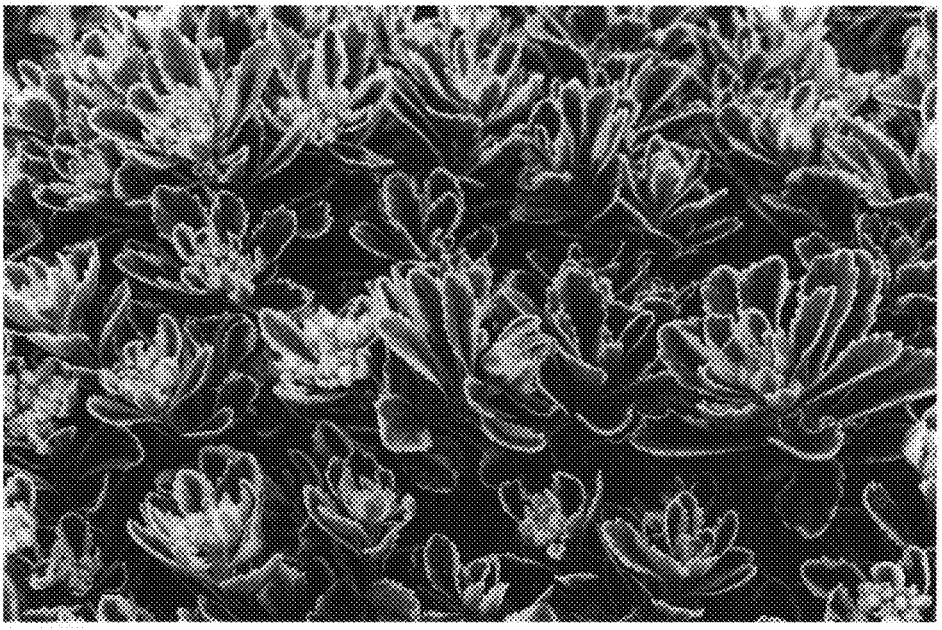
FIG. 2 shows a close-up of the foliage and young flower buds.

The following is a detailed description of one-year-old plants of the new cultivar as grown outdoors in a full sun trial plot at a wholesale nursery in Zeeland, Mich. No plant growth regulators have been used. Plants of the new cultivar have not been tested under all possible conditions. The phenotype may vary with changes in environment, climate, and cultural conditions without change however in the genotype. The color reference is in accordance with the 2015 edition of The Royal Horticultural Society Colour Chart except where general color dictionary terms are used.

Botanical designation: *Sedum* hybrid;

Cultivar denomination: 'Boogie Woogie';

Parentage: The naturally occurring branch sport of 'Little Miss Sunshine';

Asexual propagation: Stem cuttings and division;

Time to initiate roots: About two weeks;

Time to finish a 3.7 liter flowering container: About three months in the summer from a rooted 2.5 cm plug;

Root description: Thick, fleshy; freely branching; creamy white to light tan in color.

Plant habit: Winter-hardy, succulent, herbaceous perennial; low mounded; multiple stiff stems, upright to outright, arising from a dense base; flower heads freely branching; dense and full, not developing open center later in the season;

Growth rate: Moderately vigorous;

Plant size: About 9.0 cm tall and 32.0 cm wide in full flower; foliage to about 8.5 cm tall and 30.0 cm wide;

Main stems: Cylindrical; glabrous; glaucous; about 25 per plant; diameter at base about 2.5 mm, about 13 cm long from base to initial flower cymes; maintaining foliage to base of stem; internodes average about 3.5 mm;

Main stem color: Variable; blend between RHS 148C and RHS 194C frequently blushed with between RHS 59C to RH 59D, to completely RHS 59C to RHS 59D;

Lateral branches: Glaucous; about 1.5 mm diameter for lowest level branching and about 9.0 cm long;

Lateral branch color: Nearest RHS 145D;

Foliage: Opposite, simple; ovate; smooth; glabrous abaxial and adaxial; lustrous adaxial, and matte abaxial; base sessile and attenuate; apex rounded; margin crenate in distal one-half to one-third and entire in basal one-half to two thirds; about 1.2 mm thick, fleshy and succulent; to about 30.0 mm long and about 17.0 mm across near apex, average about 25.0 mm long, about 14.0 mm across at widest portion near apex, base tapering to about 1.5 mm across; decreasing in size distally;

Foliage color: Young developing leaves—adaxial center nearest RHS 137B, margin nearest RHS 8D with blush around edges of nearest RHS 60A, abaxial center between RHS N138D and RHS 191C with margin nearest RHS 158A and blush in margin of between RSH 60A and RHS 60B; fully developed leaves at flowering time—adaxial center between RHS N138C and RHS 191C, margin nearest RHS 11C with blush of between RHS 60A and RHS 60B, abaxial center between RHS N138D and RHS 191C, margin nearest RHS 158B with blush of between RHS 60A and RHS 60B;

Venation: Pinnate; color same as surrounding leaf tissue on both surfaces;

Flower: Rotate; upright; perfect; actinomophic; in terminal compound cymes; freely flowering habit with up to 21 flower buds and flowers per terminal branched cyme, 50 per branched stem and 1,000 per plant, covering nearly the entire foliage;

Flower size: About 14.0 mm across and 7.0 mm long;

Flower facing: Upward to outwardly;

Flower fragrance: Not detected;

Flowering season: Beginning early summer and continuing for about four weeks in Zeeland, Mich.;

Longevity: Individual flower remain effective for about four to six days on the plant; individual flowers persistent;

Flower buds about one day prior to opening: Broadly elliptic; apex acute; base rounded; about 8.0 mm long and 3.5 mm across;

Flower bud color: Exposed petals nearest RHS 5C;

Inflorescence: About 5.0 cm tall from first branch and 4.0 cm across; about 21 flowers per center cyme and 4 per cyme branch;

Petals: Typically six (rarely four or five), lanceolate; acute apex, base truncate and fused, margin entire, glabrous; lustrous both adaxial and abaxial; typically about 7.0 mm long and about 2.2 mm across;

Petal color: Adaxial and abaxial nearest RHS 2A;

Sepals: Typically six, lanceolate; margin entire; glabrous and lustrous abaxial and adaxial; acute apex, truncate fused base; campanulate; about 3.0 mm long and about 1.2 mm wide at fused base;

Sepal color: Nearest RHS 155A both adaxial and abaxial surfaces;

Peduncles: Glabrous; cylindrical; strong and stiff, yet flexible; freely branching; angle erect in center to nearly 60 degrees from perpendicular for branched portions; flowering portion about 5.0 cm long and 3.5 cm across;

Peduncle color: Variable; blend between RHS 148C and RHS 194C frequently blushed with between RHS 59C to RH 59D, to completely RHS 59C to RHS 59D;

Pedicels: Cylindrical; lustrous; glabrous; strong and stiff, yet flexible; to about 3.0 mm long and 0.5 mm diameter;

Pedicel color: Between RHS 148C to RHS 194C;

Androecium: Typically ten; to 6.0 mm long;

*Filaments*.—Thin; cylindrical; upright; fused to petal base; about 5.0 mm long and about 0.5 mm diameter; color nearest RHS 7B.

*Anthers*.—Ellipsoidal; basifixed; longitudinal; about 1.0 mm long and about 0.5 mm wide; color nearest RHS 13A.

*Pollen*.—Abundant; color nearest RHS 13A.

Gynoecium: Typically six, rarely four or five; cylindrical, conical in distal one third;

*Style*.—About 2.0 mm long and 0.5 mm diameter at point of attachment to ovary; glabrous; color nearest RHS 1A.

*Stigma*.—Minute; color nearest N144C.

*Ovary*.—Nearly cylindrical, tapering at apex to style; about 3.5 mm long and 1.0 mm diameter; color nearest RHS 1A.

Seed and fruit: Have not yet been observed;

Disease and pest resistance: Plants of the new *Sedum* 'Boogie Woogie' grow best with good drainage, full sun and moderate to low fertility. 'Boogie Woogie' is cold hardy from USDA zones 3 to 9. 'Boogie Woogie' tolerates heavy rains and wind and does not tend to develop an open center later in the season as many other stonecrop cultivars do. 'Boogie Woogie' is less prone to producing lethal white branch sports than 'Nonsitnal'. Other pest and disease resistance and tolerance outside that normal for stonecrop is not known.

It is claimed:

1. The new and distinct perennial *Sedum* plant named 'Boogie Woogie' as herein described and illustrated useful for landscaping as a specimen plant, en masse or as a cut flower.

* * * * *